United States Patent [19]

Ishida et al.

[11] 3,988,462
[45] Oct. 26, 1976

[54] 3-(5,7-DIMETHYL-2-HYDROXY-4-OXO-6,8-DECADIENYL)-GLUTARIMIDE AS AN ANTIVIRAL AGENT AGAINST POLIO AND A-TYPE INFLUENZA

[75] Inventors: Nakao Ishida, Sendai; Tsutomu Okada; Akira Kamata, both of Yokohama, all of Japan

[73] Assignee: Mitsubishi Chemical Industries Ltd., Tokyo, Japan

[22] Filed: Aug. 25, 1975

[21] Appl. No.: 607,421

Related U.S. Application Data

[62] Division of Ser. No. 525,222, Nov. 19, 1974, Pat. No. 3,926,731, which is a division of Ser. No. 391,996, Aug. 27, 1973, Pat. No. 3,880,858.

[30] Foreign Application Priority Data

Aug. 25, 1972 Japan.............................. 47-85074

[52] U.S. Cl................................ 424/268; 424/267
[51] Int. Cl.$^2$...................................... A61K 31/445

[58] Field of Search........................... 424/267, 268

[56] References Cited
UNITED STATES PATENTS 3,095,418  6/1963  Rao.................................. 424/268

Primary Examiner—Sam Rosen
Attorney, Agent, or Firm—Oblon, Fisher, Spivak, McClelland & Maier

[57] ABSTRACT

3-(5,7-Dimethyl-2-hydroxy-4-oxo-6,8-decadienyl)-glutarimide is prepared by cultivating *Streptomyces pluricolorescens* var. *yamashitaensis* (S-885) ATCC No. 21956 in an aqueous nutrient broth containing a carbohydrate and a source of organic nitrogen until said broth achieves substantial antiviral activity, and recovering said antibiotic from said culture broth. This antibiotic is effective against the viruses of polio and A-type influenza.

1 Claim, No Drawings

3-(5,7-DIMETHYL-2-HYDROXY-4-OXO-6,8-DECADIENYL)-GLUTARIMIDE AS AN ANTIVIRAL AGENT AGAINST POLIO AND A-TYPE INFLUENZA

This is a division of application Ser. No. 525,222, filed Nov. 19, 1974, now U.S. Pat. No. 3,926,131 which is a division of application Ser. No. 391,996, filed Aug. 27, 1973 now U.S. Pat. No. 3,880.858.

BACKGROUND OF THE INVENTION

1. Field of the Invention

The present invention relates to an antibiotic and a process for preparing the same. More particularly, the present invention relates to the antibiotic: 3-(5,7-dimethyl-2-hydroxy-4-oxo-6,8-decadienyl)-glutarimide designated as Antibiotic TS-885.

2. Description of the Prior Art

Various antibiotics and other compounds have been prepared by cultivating Streptomyces strains which include compounds such as protomycin and streptimidone which have been disclosed in the following publications:

R. R. Frohardt, H. W. Dion, Z. L. Jakubowski, A. Ryder, J. C. French, and Q. R. Bartz, *Journal of the American Chemical Society*, 81 5500(1959);

P. W. R. Woo. H. W. Dion,and Q. R. Bartz, ibid., 83 3085(1961); F. F. van Tamelen and V. Haarstad, ibid., 82,2974 (1960); Francis Johnson, N. A. Starkovsky and William D. Gurowitz, ibid., 37, 3492(1965);

R. Sugawara and A. Matsumae, *Journal of Antibiotics* 16A 111(1963). This invention is concerned with the preparation and isolation of another, previously unknown antibiotic from Streptomyces.

SUMMARY OF THE INVENTION

One object of the invention is to provide an antibiotic which is useful in suppressing the growth of a number of viruses.

Another object of the invention is to provide a process for producing the antibiotic.

These objects and other objects of the invention as hereinafter will become more readily apparent can be attained by the compound: 3-(5,7-dimethyl-2-hydroxy-4-oxo-6,8-decadienyl)-glutarimide which is effective against viruses including poliovirus and influenza virus type A. The compound can be prepared by cultivating *Streptomyces pluricolorescens* var. *yamashitaensis* S-885 which is registered at the Fermentation Research Institute of the Japanese Ministry for International Trade and Industry in Tokyo and identified as FERM-1546, and also registered at the American Type Culture Collection and identified as ATCC No. 21956 in an aqueous nutrient medium under submerged aerobic fermentation conditions.

DETAILED DESCRIPTION OF THE PREFERRED EMBODIMENTS

The original source of the organism *Streptomyces pluricolorescens* var. *yamashitaensis* is an area near Watari-gun, Miyagi Pref. Japan, and the taxonomical characteristics of the strain are as follows:

A. Morphology

The strain is well developed on both natural and synthetic media whereby vegetative base mycelium are formed. The aerial mycelium in glycerol agar and glucose-asparagine agar media forms irregularly branching main axels which produce closed spirals and which form no whorls. Further, ellipsoidal spores (0.4–0.6 × 0.9–1.2 μ) are located at the top of the aerial mycelium. The surface of the spores is smooth as observed through an electron-microscope.

B. Cultural Characteristics

The characteristics of the Streptomyces S-885 bacteria were observed in various media which are usually used for the identification of Streptomyces strains.

The results are as follows:

1. Sucrose-nitrate (Czapek's solution) agar plate medium (27° C).

The strain is characterized by a colorless growth which forms a powdery mycelium having a grey to greyish-brown color and which produces no soluble pigment.

2. Glycerol-nitrate agar plate medium (27° C).

The strain is characterized by a greyish-brown growth with a brownish-purple color on the opposite surface which forms a powdery aerial mycelium having a pale orange color and which produces a soluble pigment having a pale reddish-brown color.

3. Glucose-nitrate agar plate medium (27° C).

The strain is characterized by a pale yellowish-orange growth with a light reddish-brown color on the opposite surface which forms an aerial mycelium having a greyish-brown color and which produces a soluble plae yellowish-brown pigment.

4. Glucose-asparagine (Krainsky's medium) agar plate medium (27° C).

The strain is characterized by a pale yellowish-brown growth with a pale yellowish-brown color on the opposite surface which forms a powdery aerial mycelium having a brownish-white color and which produces a pale yellowish-pigment.

5. Ca-malate agar plate medium (27° C).

The strain is characterized by a blackish-brown growth with a dark brown color on the opposite surface at 27° C which forms a powdery aerial mycelium having a pale yellow-to-pale orange color and which produces a soluble greyish-orange colored pigment.

6. Starch agar plate medium (27° C).

The strain is characterized by a light reddish-yellow growth with a reddish-yellow color on the opposite surface which forms a powdery aerial mycelium having a brownish-white color and which produces a soluble orange-colored pigment.

7. Tyrosine agar plate medium (27° C).

The strain is characterized by a greyish-brown growth with a pale greyish-orange color on the opposite surface which forms an aerial mycelium having a pale orange color and which produces a soluble pale yellowish-brown pigment.

8. Glucose-Czapek's solution (27° C).

The strain grows in the form of a cinnamon pellicle, produces no aerial mycelium and forms a soluble brownish pigment.

9. Cellulose agar medium (27° C).

The strain grows poorly and does not produce either an aerial mycelium or a soluble pigment.

10. Nutrient agar slant medium

The strain is characterized by a colorless to greyish-white growth with a pale yellowish brown color on the opposite surface and which produces neither an aerial mycelium nor a soluble pigment.

11. Peptone-glucose agar medium (37° C).

The strain is characterized by a dark orange-colored growth with a reddish-yellow color on the opposite surface, and which forms poor greyish-white mycelium while producng no soluble pigment.

12. Blood agar plate medium (37° C).

The strain is characterized by a greyish-yellow-to-yellow growth and produces neither an aerial mycelium nor a soluble pigment.

13. Egg agar medium (37° C).

The strain grows poorly as a yellow growth and produces neither an aerial mycelium nor a soluble pigment.

14. Gelatin Stab medium (20° C).

The strain is characterized by a pale brownish growth and produces no aerial mycelium but produces a soluble pale reddish-brown pigment.

15. Litmus milk medium (37° C).

The strain is characterized by a pale yellowish-brown, ring-shaped growth and produces an aerial mycelium which turns a dull red color in a liquid and which shows an acidic pH.

16. Loeffer's serum medium (37° C).

The strain is characterized by a creamy to pale yellowish-brown growth as a colony with an elevated center. It produces no aerial mycelium and changes to a pale yellow color when cut into pieces.

C. Utilization of carbon sources

Tests in various media have shown that the Streptomyces bacterium utilizes basic media, Pridham and Gottlieb's basal salts media, arabinose, glucose, glycerol, maltose, mannitol, mannose and starch very well as carbon sources. Fructose, lactose, and sucrose are assimilated but rhamnose, xylose and inositol are not utilized as a carbon source by the strain.

D. Physiological Properties

The strain has a positive Ca-malate solubility, nitrate reduction, starch hydrolysis, gelatin liquefaction, serum liquefaction, and milk ocagulation and liquefaction. However, the strain exhibits a negative tyrosinase reaction and melanin formation.

E. Growth temperature and pH

The optimum temperature for growth of the bacterium is 27° C and the strain grows well at 27° C in a media with a pH of 6–8.4. It can also be grown at 15°–37° C in media having a pH of 7.0–8.0 but does not grow at temperatures higher than 60° C at any pH. The strain is aerobic.

From the various taxonomical properties exhibited by the bacterium, it can be concluded that the strain is similar to *Streptomyces pluricolorescens Okami* et Umezawa, but differs from it in some detail. The taxonomical properties of *Streptomyces pluricolorescens Okami* et Umezawa have been disclosed in the Journal of Antibiotics, Series A Vol. 19 pages 1–9 (1966). A comparison of the properties of the two bacterium show that Streptomyces S-885 differs from *Streptomyces pluricolorescens* in that pluricolorescens grows only in linear chains having tuft-like branches and is characterized by a colorless growth in a gelatin stab medium which produces a pale brown colored aerial mycelium and which produces no soluble pigment. These properties are clearly inferior to the properties exhibited by Streptomyces S-885, and certain other properties are also slightly different. From the data obtained it can be concluded that Streptomyces S-885 is a variety of *Streptomyces pluricolorescens* and is, therefore, designated as *Streptomyces pluricolorescens* var. *yamashitaensis*.

Antibiotic TS-885 can be produced by culturing an antibiotic TS-885 producing organism which belongs to a natural or synthetic Streptomyces genus. However, the process of the invention is not limited to this method of production since a variety of known culturing processes for actinomycetales can be conveniently applied for industrial use. It has been found that the bacterium can be effectively grown by a culture process in a fermentation tank. During the culture process, the pH of the medium is preferably 6–8 and the temperature is in the range of 25°–30° C, especially 27°–28° C.

Suitable growth media can be prepared from conventional materials used for actinomyceltales cultures such as various carbon sources, nitrogen sources, inorganic salts, antifoaming agents, and the like and combinations thereof. Molasses, glycerin and glucose are the optimum carbohydrate sources, although starch, sucrose, maltose lactose, dextrin, cellulose and fructose can also be employed. When the medium uses a carbohydrate source, concentration of the carbohydrate is in the range of 0.5–10% by weight, preferably 1–5% by weight of the total medium. Meat extract, peptone and CSL use the optimum nitrogen sources, although soybeans, casamino acid, polypeptones, ammonium sulfate, potassium nitrate, and casein can also be employed. When the medium uses a nitrogen source, the concentration of the nitrogen source is in the range of 0.3–5% by weight, preferably 0.5–3% by weight of the total medium. The inorganic salt nutrients include the usual salts which yield potassium, magnesium and phosphate ions. The concentration of the inorganic salts in the growth medium should range from 0.01–1% by weight of the total medium. Preferably, silicone oil or soybean oil is added as the antifoaming agent.

The maximum accumulation of the antibiotic TS-885 occurs after 48–120 hours from the initiation of cultivation. The amount of antibiotic TS-885 accumulated in the culture broth can be measured by the following two methods:

a. a method whereby the growth of Helacells is inhibited, and b. a method whereby plaque formation of polio virus in Helacells is inhibited.

When the bacterial culture broth is treated to separate the liquid phase from the solid containing mycelia by conventional processes such as filtration or centrifugal separation, Antibiotic TS-885 is chiefly present in the culture filtrate although small portions of the antibiotic remain with the solid. In order to isolate Antibiotic TS-885, it can be effectively extracted with an organic solvent such as ethyl acetate, amylacetate, butanol, or the like because the antibiotic is water insoluble. Antibiotic TS-885 extracted with the organic solvent can be further purified by column chromatography or thin layer chromatography on silica gel, alumina or Florisil or a column of Sephadex LH-20.

In one embodiment of the separation process the culture broth is filtered to remove the solid component and hydrochloric acid is added to the filtrate to adjust the pH. antibiotic TS-885 is then extracted with an organic solvent such as ethylacetate from the culture filtrate. The solvent is evaporated at temperatures lower than 40° C in vacuo to concentrate Antibiotic TS-885. The resulting dark brown, oily product is then developed by silica gel column chromatography with (1) benzene, (2) ethylacetate and (3) ethanol, in that order whereby a yellow band, a yellowish-red band and a brown band form on the column. The yellow band is eluted from the column with benzene and it is inactive. As the concentration of ethylacetate is increased in the eluting solution, the eluted band becomes unclear, and most of Antibiotic TS-885 is eluted when a mixture of benzene and ethylacetate (1 : 1 by weight) is used. The resulting yellow mixture containing Antibiotic TS-885 is further purified by silica gel column chromatography. In the purification process the resulting mixture is developed with benzene to remove impurities and then the active principle is eluted with a mixture of benzene and ethylacetate (4 : 1). From the yellowish syrup, Antibiotic TS-885 is finally purified by thin layer chromatography (developer:ethylacetate) to separate the fraction having an Rf value of 0.5. Antibiotic TS-885 is obtained as a pale yellowish viscous material. The resulting yellow viscous product is further developed by thin layer chromatography (developer:ethylacetate) to separate a fraction having an Rf value of 0.5 whereby a purer, pale yellow viscous Antibiotic TS-885 is obtained.

Structural identification studies have shown that Antibiotic TS-885 is 3-(5,7-dimethyl-2-hydroxy-4-oxo-6,8-decadienyl)-glutarimide which has the formula:

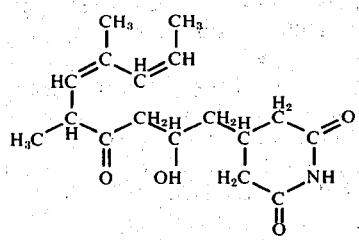

The physico-chemical properties of the compound are as follows:

(1) Form
Weakly Acidic, pale yellowish oily material.
(2) Elementary Analysis: [$C_{17}H_{25}O_4N$]

| | Calculated | Found |
|---|---|---|
| C% | 66.42 | 65.88 |
| H% | 8.20 | 8.60 |
| N% | 4.56 | 4.38 |
| O% | 20.82 | 21.14 |

(3) Molecular Formula
$C_{17}H_{25}O_4N$
(4) Molecular weight
307(mass spectrography) [$M^+$, m/e = 307]
(5) Specific rotary power
$[\alpha]_D^{27} = +105°$ (C: 0.1, $CHCl_3$)
(6) Boiling Point
135° C – 140° C (1 mm/Hg)
(7) Color Reaction
Positive Ehrlich reaction, m-phenylenediamine reaction (active methylene) and carbon bisulfide reaction (primary and secondary amine).
Negative Tollens and ninhydrin reactions.
(8) Solubility
Soluble: acetone, chloroform, benzene, ethylacetate, ethanol, methanol; 1% aqueous sodium hydroxide solution, and pyridine.
Sparingly soluble: ether
Insoluble: water and a 5% aqueous hydrochloric acid solution.
(9) Rf values on a thin layer chromatography plate using various solvents.
0.8 (chloroform: ethanol = 10 : 3)
0.65 (ethanol)
0.5 (ethylacetate)
0.25 (benzene: ethylacetate = 1 : 1)
0 (benzene)

The physiochemical properties of Antibiotic TS-885, Streptimidone and Protomycin are shown in Table 1.

| | Physicochemical Properties of Antibiotic TS-885, Streptimidone and Protomycin | | |
|---|---|---|---|
| Properties | Antibiotic TS-885 | Streptimidone | Protomycin |
| Form | pale yellowish oil | Colorless needles | white crystals |
| M.P.(B.P) | 135–140° C/1 mmHg | 72–73° C | 58–61° C |
| $[\alpha]_D$ | +105° (C 0.1, $CHCl_3$) | +238° (C 0.5, $CHCl_3$) | +126° (C 1.0, $CHCl_3$) |
| Solubility | Soluble in benzene, ethyl acetate, acetone, ethanol 1% NaOH: Sparingly soluble in ether: insoluble in water 5% HCl: | Soluble in benzene, ethyl acetate, acetone, ethanol: insoluble in water: | Soluble in benzene, ethyl acetate, acetone, ethanol: insoluble in $CCl_4$ petroleum ether: |
| Mol. Formula | $C_{17}H_{25}O_4N$ | $C_{16}H_{23}O_4N$ | $C_{19}H_{29}O_5N$ |
| Mol. Wt. | 307 | 293 | 351 |
| U.V. $\lambda$max nm ($\epsilon$) | 231.5(15,350) 283.0(1,259) 291.0(1,230) | 232(23,100) 291( 790) | 232.5(24,000) 287 ( 1,330) |
| IR: $cm^{-1}$ | 3475, 3225 1725, 1710 1690 | 3575, 3425 1710, 1700 1680 | 3475, 3350 1725, 1690 |
| N.M.R. Spectrum | 1.15(>CH—$CH_3$) 1.8 (C=CH—$CH_3$) 1.85(C=C—$CH_3$) | 1.07(>CH—$CH_3$) 1.83(C=C—$CH_3$) | |
| Mass Spectrum | $M^+$, m/e = 307 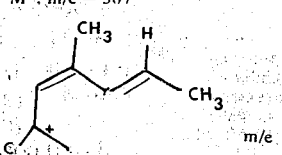 m/e 109 | | |

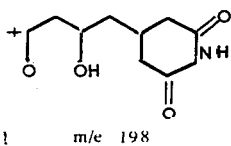

m/e 198

The formula of Antibiotic TS-885 was confirmed by the data obtained wherein the infrared adsorption spectrum indicates the presence of —OH, and —NH— and keto groups and a conjugated double bond. The ultraviolet adsorption spectrum of the antibiotic indicates the presence of a conjugated double bond, and a glutarimide ring while the N.M.R. spectrum indicates the presence of three methyl groups in the compound. The characteristic activities of the Antibiotic TS-885, 3-(5,7-dimethyl-2-hydroxy-4-oxo-6,8-decadienyl)-glutarimide, are as follows:

A solution containing Antibiotic TS-885 was prepared as follows to determine the biological activity of Antibiotic TS-885. A 100 mg amount of 3-(5,7-dimethyl-2-hydroxy-4-oxo-6,8-decadienyl)-glutarimide (Antibiotic TS-885) was dissolved in a mixture of 0.6 ml of dimethyl-sulfoxide and 0.02 ml of polyoxyethylene sorbitane monolaurate (EO : 20). A 1.0 ml amount of a stirred saline solution (0.01 M phosphate buffered saline, pH 7.2) was added to the mixture to form a uniform solution which was followed by the addition of 48 ml of the saline solution. By this procedure a stock solution of Antibiotic TS-885 having a concentration of 2 mg/ml was prepared. The stock solution was diluted with the buffer solution for the following tests.

1. Antimicrobial activity

Antibiotic TS-885 exhibits no antibacterial and antimycoplasmal activity. However, it showed inhibitory activity against some yeasts. The antimicrobial spectra were observed by the pulp disc diffusion method and the agar streak method, and the results are shown in Tables II and III.

TABLE II

| Test organism | medium *1 | Minimum inhibitory concentration (mcg/ml) |
|---|---|---|
| Staphylococcus aureus 209p | N | >1000 |
| Streptococcus hemolyticus | N | '' |
| Diplococcus pneumoniae | N | '' |
| Sarcina lutea 1001 | N | '' |
| Bacillus subtilis | N | '' |
| Escherichia coli NIHJ | N | '' |
| Shigella flexneri 2a | N | '' |
| Proteus mirabilis | N | '' |
| Pseudomonas aeruginosa | N | '' |
| Salmonella typhi | N | '' |
| Candida alibicane | E | '' |
| Trychophyton rubrum | E | 1000 |
| Mycoplasma pneumoniae | PPLO-agar | >1000 |
| Mycoplasma hominis | '' | '' |
| Mycoplasma orale | '' | '' |
| Mycoplasma salivarium | '' | '' |
| Mycoplasma gallisepticum | '' | '' |
| Mycoplasma laidlawii | '' | '' |

*1 Medium
N: Nutriene agar medium
E: Yeast extract medium
PPLO-agar Hayflicks PPLO complete medium (Difco) +0.5 % yeast extract and 20 % horse serum globulin

TABLE III

| Test Organism | Medium | Minimum inhibitory concentration (mcg/ml) |
|---|---|---|
| Candida albicans | S.A. | >100 |
| Candida utilis IFO 0396 | S.A. | 100 |
| Candida tropicalis | M.A. | 100 |
| Candida parapsiiosis IFO 0708 | M.A. | >100 |
| Hansenula anomala IFO 0118 | '' | 20 |
| Cryptococcus albidus IFO 0378 | '' | 4 |
| Brettanomyces anomalus IFO 0648 | '' | >100 |
| Phodotorula glutinis IFO 0754 | '' | 100 |
| R. rubra IFO 0001 | '' | 20 |
| Torula rubra var alpa | '' | 4 |
| Saccharomyces sake HUT 7119 | '' | 4 |
| Saccharomyces fragilis IAM 7160 | '' | 20 |
| Saccharomyces rosei AHU 3174 | '' | 100 |

Medium:
S.A. Sabouraud's agar
M.A. Malt Agar

2. Cytotoxicity

The cytotoxicity of Antibiotic TS-885 against various tissue culture cells was observed by the following two methods:
a. a cylinder method (on a thin seed plate)
b. a tube dilution method a. A 10 ml amount of a cell suspension ($3 \times 10^5$ cells/ml) was seeded in a petri dish having a diameter of 90 mm. The plates were incubated in a $CO_2$ incubator at 37° C.

After 24 hours, the medium was removed and the plates were overlaid with 5 ml of an agar medium and one cylinder was placed on the medium. A 0.25 ml amount of a test sample was placed in the cylinder. After maintaining the plates for 2 hours at room temperature to diffuse Antibiotic TS-885 into the agar, the plate was incubated in the $CO_2$ incubator at 37° C. After 48 hours, the cytotoxic effect of Antibiotic TS-885 was determined by the size of the diameter of the growth inhibitory zone around the cylinder. (2) In the tube dilution method, $2 \times 10^5$ cells were inoculated into a small test tube, and the tubes were incubated at 37° C for 24 hours. Solutions containing various concentrations of Antibiotic TS-885 were added to tubes of the cells and reincubated at 70° C. After 48 hours, the degenerated cells were microscopically observed. The results are shown in Table IV.

TABLE IV

| Test cells | Medium | Minimum Inhibitory Concentration | |
|---|---|---|---|
| | | cylinder method | tube dilution method |
| HeLa(Hela S₃ cells) | YLE | 0.2 | 0.4 |
| L(L-cells) | YLE | 0.25 | 0.5 |
| CEC(chick embryo fibroblast cells) | MEM | 0.5 | 1.0 |
| MK(monkey kidney cells) | MEM | 0.2 | 0.4 |
| P₃HR-1 (Burkitt lymphoma cells) | MEM | — | 0.4 |

3. Antiviral activity

A. The inhibitory activity of the antibiotic which prevents the multiplication of polio virus in HeLa cell cultures was determined.

1. Tube dilution method

A 400,000/ml quantity of HeLa cells was inoculated into a small test tube and the cells were cultured at 27° C for 48 hours. The HeLa cells culture was infected with approximately 100 TCID 50/ml of poliovirus. After incubation at 37° C for 90 minutes whereby the virus was absorbed in the cells, the cells were washed with Hanks solution and the solution of various concentrations of Antibiotic TS-885 were added. After incubation at 37° C for 48 hours, the cytopathic effect upon the cells was microscopically observed. The results are shown in Table V.

TABLE V

| Concentration (mcg/ml) | Cytotoxicity | Cytopathic effect | Antiviral effect |
|---|---|---|---|
| 10 | + | − | Toxic |
| 1 | + | − | Toxic |
| 0.5 | + | − | Toxic |
| 0.25 | − | − | − |
| 0.125 | − | + | + |
| 0.0025 | − | − | − |
| 0 | − | ++++ | − |

2. Plate method

Ten ml of Hela cells ($6 \times 10^5$ cells/ml) were seeded in a petri dish (90 mm diameter) and the plates were incubated in a $CO_2$ incubator at 37° C. After 24 hours, the plates were infected with poliovirus at 1,000 P Fu/ml. After incubation at 37° C for 120 minutes to absorb the virus, the plates were washed with two parts of Hank's salt solution to remove the unabsorbed virus. The plates were then overlaid with 5 ml of an agar medium, and a pulp disc containing various concentrations of Antibiotic TS-885. The antiviral activity was measured from the diameter of the plaque free zone by the pulp disc diffusion method. The results are shown in Table VI.

TABLE VI

| Concentration (mcg/ml) | plaque free Cytotoxicity | Diameter of Antiviral zone | effect |
|---|---|---|---|
| 25 | + | 36.0 | toxic |
| 12.5 | − | 29.2 | toxic |
| 6.25 | − | 28.4 | − |
| 5.0 | − | 25.0 | − |
| 1.0 | − | 19.4 | + |
| 0.5 | − | 15.0 | + |
| 0 | − | 0 | − |

B. The antiviral effect of the antibiotic on the vesicular stomatitis virus was determined in a test tube containing chick embryo fibroblast cells infected with the Vesicular stomatitis virus. The plaque method was used to measure the antiviral effect. The results are shown in Table VII.

Table VII

| Concentration (mcg/ml) | Cytotoxicity | Diameter of plaque free zone (mm) | Antiviral effect |
|---|---|---|---|
| 250 | + | 42.0 | toxic |
| 125 | + | 33.2 | toxic |
| 100 | + | 31.7 | toxic |
| 62.5 | + | 28.8 | toxic |
| 20 | + | 26.2 | toxic |
| 10 | − | 22.9 | + |
| 5 | − | 19.6 | + |
| 2.5 | − | 18.9 | + |
| 1.25 | − | 18.1 | + |
| 0.6 | − | 17.4 | + |
| 0.3 | − | 15.4 | + |
| 0 | − | >8.0 | / |

C. The antiviral effect of the antibiotic on influenza virus in mice was measured. Antibiotic TS-885 was administered intraperitoneally to the mice 6 hours and 3 hours before infection with the virus. The mice were treated 3 hours, 6 hours and once daily for 7 successive days with dosages of 7 or 22 mg/kg after infection with the influenza virus. The mice were infected with the virus (influenza virus-$A_2$/Kumamoto, $10LD_{50}$) by inhalation. The antiviral effect was determined by the prolongation of the life of the mice in comparison with untreated mice and/or Amantadine (1,Adamantylamine) treated mice. The results are shown in Table VIII.

TABLE VIII

| Survival days | Survival / treated × 100 % | | | |
| | Antibiotic TS-885 | | Amantadine | Control |
| | 22 mg/kg | 7 mg/kg | 20 mg/kg | |
|---|---|---|---|---|
| 7 | 100 % | 100 % | 100 % | 100 % |
| 10 | 80 % | 60 % | 60 % | 45 % |
| 13 | 50 % | 35 % | 10 % | 10 % |
| 15 | 50 % | 35 % | 0 % | 0 % |
| 20 | 50 % | 35 % | 0 % | 0 % |

When Antibiotic TS-885 was administered at a dosage rate of 22 mg/kg. a survival rate of 50% was observed showing the antiinfluenza effects of the antibiotic.

D. Antitumor effect 1,000,000 mouse ascites tumor cells (Sarcoma 180) were transplanted intraperitoneally into mice. 24 Hours after the mice were treated with the transplanted tumor cells, the mice were injected with various doses of the antibiotic once daily for six days intraperitoneally. Antibiotic TS-885 inhibits growth of the ascites tumor at doses of 2.5 mg/mouse per day. It is that the life span of the antibiotic treated mice was prolonged.

E. In vivo and in vitro tests

Antibiotic TS-885 was injected into intravenously mice at dosages of 2.5 mg/kg and 25 mg/kg. Ten minutes and thirty minutes after injection, the mice were sacrificed and the serum was obtained. The concentration of the antibiotic in the serum was measured by the inhibitory effect on plaque formation of poliovirus in Hela cells. The results indicate that the group of mice to which 25 mg/kg of the were administered had a concentration of 2.9 meg/ml after 10 minutes and 2.4 meg/ml after 30 minutes of the antibiotic in the blood. The group injected with the 2.5 meg/ml of the antibiotic had a concentration of 1.8 meg/ml after 10 minutes and 0.58 meg/ml after 30 minutes of the antibiotic in the blood.

6. Toxicity

No signs of toxicity were observed when Antibiotic TS-885 was administered once daily for 10 days at a dosage rate of 20 mg/kg per day by the intravenous injection of mice having a body weight of 20 g (total dosage is 200 mg/kg).

Antibiotic TS-885 can be administered to animals to prevent or inhibit infections of poliovirus, influenza virus type A, or the like. When administered prior to infection, that is prophylactically, it is preferred that the antibiotic be administered with 0 to 24 hours prior to infection of the animal with the pathogenic virus. The antibiotic can be administered topically, orally or parenterally to a mammalian host such as for example, monkeys, dogs, cats and guinea pigs which have been infected with one of the viruses. The optimum dosage will vary with the form of administration; the virus for which treatment is desired,; the type of animal involved, its age, health and weight,; the extent of infection; the frequency of treatment and the nature of the effect desired. A suitable dosage regimen of from 0.5–20 mg/kg body weight can be administered.

Among the dosage forms which can be used for oral or parenteral administration are, for example, tablets, capsules and injections all of which are well known to the pharmacist. The antibiotic may also be administered, dissolved or suspended in any conventional nontoxic pharmaceutical carrier of the type that may be taken orally, applied topically, buccally or parenterally.

Having generally described this invention, a further understanding can be obtained by reference to certain specific examples which are provided herein for purposes of illustration only and are not intended to be limiting unless otherwise specified.

EXAMPLE 1

A 100 ml amount of a liquid medium having a pH of 7.2 which comprises 2% soybean, 0.5% sodium chloride, 0.2% calcium carbonate, 2% starch, 0.005% manganese sulfate, 0.005% zinc sulfate, and 0.005% cupric sulfate was charged into a 500 ml agitated flask and 1 loopful of Streptomyces S-885 (ATCC-21956) was innoculated and then cultured with agitation at 37° C for 20 hours to prepare the seed. In addition, a 250 ml medium having a pH of 7.4 which comprises 1% peptone, 0.5% bouilon, 0.5% sodium chloride, 0.2% calcium carbonate, 1% glycerin and 3% starch was divided into 200 portions and each portion in 3 ml amounts was added to a separate agitated 500 ml flask at an aerobic culture temperature of 27° C. The accumulation of Antibiotic TS-885 in the culture broth reached a maximum at about 96 hours. The titer of the broth was about 100 mcg/ml and the pH of the broth was about 8.2. The culture was then stopped and the solid component was filtered with a filter paper or a filtering agent in order to obtain about 220 ml of a yellowish brown filter paper in a filtering agent adjusted to a pH of 5.0 with hydrochloric acid, and was extracted with ethylacetate (half the amount of the filtrate) two times whereby the most active principle was extracted in the ethylacetate layer. The resulting ethylacetate layer was concentrated at a temperature lower than 40° C in vacuo to remove ethylacetate whereby 2.4 g of a crude dark brown oily material containing Antibiotic TS-885 was obtained. The crude oily material inhibited the growth of HeLa cells at a concentration of 1.2 mcg/ml, and the titer of the product was 350 mcg/mg.

EXAMPLE 2

A 2.4 g amount of the dark brown oily material prepared in accordance with Example 1 was charged into a column with a diameter of 3 cm and a length of 50 cm containing 60 g of silica gel and a dry, chromatographic separation was conducted. The column was developed with 1000 ml of benzene and a yellow impurity was eluted. The active fraction was eluted with a mixture of benzene and ethylacetate (1:1) 900 mg fraction of a yellowish brown syrup containing Antibiotic TS-885 was obtained which is active to HeLa cells. The titer of the product was 700 mcg/mg.

EXAMPLE 3

The yellowish brown crude Antibiotic TS-885 prepared in accordance with Example 2 was further purified by rechromatography using a silica gel column. A 900 mg amount of the crude material was dissolved in 2 ml of benzene and was applied to a column (diameter of 3 cm and length of 60 cm) filled with 70 g of silica gel. The column was developed with 1200 ml of benzene. Subsequently, ethylacetate was added to benzene, and the mixture was used for the elution to remove most of the impurities. The column was further developed with 1500 ml of a mixture of benzene and ethyl acetate (4 : 1) to elute all of Antibiotic TS-885. The eluate was concentrated in vacuo and the solvent was evaporated whereby a 385 mg amount of yellow antibiotic TS-885 was obtained. The titer of the product was 900 mcg/mg.

EXAMPLE 4

The yellow Antibiotic TS-885 prepared in accordance with Example 3 was finally purified by thin layer chromatography. About 10 g of silica gel (Merk Kiesel gel) was coated on a plate (20 × 20 cm) and dried and activated. About 30 mg of Antibiotic TS-885 dissolved in acetone was applied to the plate and the antibiotic was developed with ethylacetate. Antibiotic TS-885 was developed at a position with an Rf value of 0.5. The spot on the plate with an Rf value of 0.5 was gathered, placed in a column (2 × 30 cm) and eluted with acetone whereby 308 mg of pure Antibiotic TS-885 was obtained. The titer of the product was 1000 mcg/mg.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for alleviating the symptoms of A type influenza or polio in a mammalian host which comprises administering to said host an antivirally effective amount of 3-(5,7-dimethyl-2-hydroxy-4-oxo-6,8-decadienyl)-glutarimide.

* * * * *